US00PP18574P3

(12) United States Plant Patent
Yencho et al.

(10) Patent No.: US PP18,574 P3
(45) Date of Patent: Mar. 11, 2008

(54) ORNAMENTAL SWEETPOTATO PLANT NAMED 'SWEET CAROLINE BEWITCHED PURPLE'

(50) Latin Name: *Ipomoea batatas*
Varietal Denomination: Sweet Caroline Bewitched Purple

(75) Inventors: George Craig Yencho, Raleigh, NC (US); Kenneth Pecota, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 11/395,062

(22) Filed: Mar. 31, 2006

(65) Prior Publication Data

US 2007/0143897 P1 Jun. 21, 2007

Related U.S. Application Data

(60) Provisional application No. 60/752,486, filed on Dec. 21, 2005.

(51) Int. Cl.
*A01H 5/00* (2006.01)

(52) U.S. Cl. ..... Plt./258

(58) Field of Classification Search ..... Plt./258
See application file for complete search history.

(56) References Cited

U.S. PATENT DOCUMENTS

2007/0143897 P1 * 6/2007 Yencho et al. ..... Plt./258

* cited by examiner

*Primary Examiner*—Wendy C. Haas
*Assistant Examiner*—Georgia Helmer
(74) *Attorney, Agent, or Firm*—Myers Bigel Sibley & Sajovec P.A.

(57) ABSTRACT

*Ipomoea batatas* 'Sweet Caroline Bewitched Purple' is an erect to semi-erect, bunch-type cultivar producing many shoots and having very dense foliage. This cultivar is distinguishable from other cultivars by its large, reniform, toothed, purple leaves and erect to semi-erect architecture. The plant has good vigor, is very well branched and produces an attractive, round mound of foliage. It is well suited for container production and/or ground cover or border applications. The production of flowers by 'Sweet Caroline Bewitched Purple' is limited even under short day conditions.

2 Drawing Sheets

Latin name of the genus and species: The Latin name of the novel, ornamental plant variety disclosed herein is *Ipomoea batatas* (L.) Lam.

Variety Denomination: The inventive cultivar of *Ipomoea batatas* disclosed herein has been given the varietal denomination 'Sweet Caroline Bewitched Purple'.

BACKGROUND OF THE INVENTION

*Ipomoea species* are members of the morning glory family Convolvulaceae. *Ipomoea batatas,* the cultivated species, is commonly produced for consumption and referred to as the white or yellow sweetpotato and the orange yam. The plants are typically fast growing, green vines possessing a wide variety of leaf shapes ranging from palmate and deeply lobed, to cordate or triangular shaped leaves with no lobes. Ornamental sweetpotates, which have been bred and selected for their unique foliage colors, leaf shapes and plant habits, typically do not produce large fleshy storage roots like the sweetpotato cultivated for consumption. In comparison, storage roots produced by ornamental sweetpotatoes are typically not as large because no selection has been exercised for yield, thus storage roots do not begin to swell until very late in the season. Further, the few storage roots that are formed by ornamental sweetpotatoes are typically not as attractive as those produced by the table-stock types as they are generally cracked, very malformed, often mottled in skin and flesh color, and are not palatable.

Late in the growing season when day-lengths begin to shorten or when the plants are stressed, ornamental sweetpotato plants produce tubular flowers that are similar to morning glories, but most plantings are dominated by the appearance of the foliage. The plants are highly desirable due to their ability to grow under varied stress conditions, cover a large space, and last the entire growing season. Moreover, these plants have few insect or disease problems.

Until the release of the Sweet Caroline series of ornamental sweet potatoes (see below) there were six popular types of *Ipomoea batatas* ornamental sweetpotatoes being cultivated primarily for their annual, summer vines in landscaping applications. These six cultivars are: 'Blackie' (not patented), having purple foliage and lavender flowers; 'Terrace Lime' (not patented) and 'Margarita' (not patented; also known as 'Sulfur'), which have large brilliant chartreuse leaves and lavender blooms; 'Black Heart' (not patented; also known as 'Ace of Spades'), having heart-shaped leaves with burgundy purple color; 'Tricolor' (not patented; also known as 'Pink Frost'), a variegated plant having pale green, white, and pink-margined leaves; and 'Lady Fingers' (unpatented), which has medium green, dainty leaves divided into long, thin, fingerlike lobes that are complemented by burgundy stems and veins.

*Ipomoea batatas* 'Margarita' was recently released in the United States, and has become widely used as a landscape annual. However, it is not suitable for mixed containers as this variety exhibits a very vigorous growth and tends to out-compete other species. See Armitage, A. M. and J. M. Garner, (2001) *Ipomoea batatas* 'Margarita'. Hort Science 36:178. Another popular variety, 'Blackie', is a vigorous purple-leaved clone, which is also unsuited to containerized gardens.

Therefore, to meet the current horticultural demand, it is desirable to produce new, more robust cultivars of ornamental sweetpotato with attractive foliage colors, leaf shapes, and plant architectures. In addition, it would be advantageous to develop cultivars of ornamental sweetpotato exhibiting a more compact growth, and which do not out-compete other species in mixed containers.

*Ipomoea batatas* 'Sweet Caroline Light Green' (U.S. Plant Pat. No. PP15,028, issued Jul. 20, 2004), 'Sweet Caroline Green' (U.S. Plant Pat. No. PP15,056, issued Aug. 3, 2004), 'Sweet Caroline Bronze' (U.S. Plant Pat. No. PP15,437, issued Dec. 21, 2004), 'Sweet Caroline Purple' (U.S. Plant Pat. No. PP14,912, issued Jun. 15, 2004), and 'Sweet Caroline Red' (U.S. Plant Pat. Publication No. PP17, 483, issued Mar. 13, 2007) are recently introduced cultivars developed at North Caroline State University that are characterized by compact growth habit, moderate to deeply lobed palmate leaves, and attractive foliage color.

The present invention relates to a new and distinct variety of *Ipomoea batatas* named 'Sweet Caroline Bewitched Purple'. This variety is an erect to semi-erect, bunch-type variety producing many shoots and having very dense foliage. This variety is distinguishable from other varieties by its large, reniform, slightly toothed, purple leaves and erect to semi-erect architecture. The plant has good vigor, is very well branched and produces an attractive round mound of foliage. It is well suited for container production and/or ground cover or border applications.

Lineage. The *Ipomoea batatas* 'Sweet Caroline Bewitched Purple' cultivar (breeding designation NC1124-3ORN) originated from a conventional cross between *Ipomoea batatas* cultivars NC547ORN (the female parent; not patented) and 'Pink Frost' (the male parent) conducted from October 2001 to April 2002 at Raleigh, N.C.

NC547ORN resulted from across between NC102-1ORN (female parent; not patented) and NC125-1ORN (male parent; not patented). Seed from this cross were planted in the Horticultural Greenhouses in Spring 2002. The parental strains used to produce 'Sweet Caroline Bewitched Purple' were NC547ORN (female parent) and 'Tricolor' (also called 'Pink Frost', male parent). 'Tricolor' is a pink, white and green variegated plant with modest vigor and moderately lobed leaves. NC547ORN is a moderately branched, thick stemmed, upright, compact plant with slightly lobed, purple-green leaves. The single, individual plant not known as *Ipomoea batatas* 'Sweet Caroline Bewitched Purple' was selected in August and September 2002 because of its combination of exceptional features and has been propagated asexually since that time.

Asexual Reproduction. Since its selection, *Ipomoea batatas* 'Sweet Caroline Bewitched Purple' has been asexually reproduced at, Raleigh, N.C., predominantly by vegetative propagation of vine cuttings. Successively, there have been three cycles of vegetative propagation, one cycle of tissue culture micropropagation, and multiple vegetative propagation cycles to increase the plant population. Asexual reproduction of the new Ornamental Sweetpotato cultivar by cuttings has shown that the unique features of the new cultivar are stable and the plant reproduces true to type in successive generations of asexual reproduction.

SUMMARY OF THE INVENTION

*Ipomoea batatas* 'Sweet Caroline Bewitched Purple' is an erect to semi-erect, bunch-type cultivar producing many shoots and having very dense foliage. This cultivar is distinguishable from other cultivars of its large, reniform, toothed, purple leaves and erect to semi-erect architecture. The plant has good vigor, is very well branched and produces an attractive, round mound of foliage. It is well suited for container production and/or ground cover or border applications. The production of flowers by 'Sweet Caroline Bewitched Purple' is limited even under short day conditions.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas*.

DETAILED BOTANICAL DESCRIPTION

The following is a detailed description of the botanical characteristics of the new and distinct cultivar of *Ipomoea batatas* plant known by the cultivar name 'Sweet Caroline Bewitched Purple'. All colors cited herein refer to The Royal Horticultural Society Colour Chart (The Royal Horticultural Society, London, 1995 edition) designations except where general terms of ordinary dictionary significance are used. Where dimensions, sizes, colors, and other characteristics are given, it is to be understood that such characteristics are approximations of averages set forth as accurately as practicable.

The descriptions reported herein are from 11-week-old specimens. *Ipomoea batatas* 'Sweet Caroline Bewitched Purple' has not been observed under all possible environmental conditions; therefore, the phenotype may differ somewhat with variations in the environment such as season, temperature, light intensity, day length, cultural conditions, and the like, without however any variance in the genotype.

Technical Description of the Variety.

Above-Ground structure. *Ipomoea batatas* 'Sweet Caroline Bewitched Purple' is a round, compact mounding plant. Long petioles allow the sinuate, reniform leaves to arch up and outward and the multiple secondary laterals results in very dense foliage. Plant height is 20 cm and the area of spread is 58 cm. 'Sweet Caroline Bewitched Purple' is a fast grower with good vigor.

Branching habitat. Very free branching with no basal shoots; however, adventitious roots develop at the nodes and will root if in contact with the soil.

Lateral shoots. The number of lateral shoots averages around 7 and each main stem has 4–6 shorter secondary shoots. Lateral branch length: ~28 cm. Diameter: 0.6 cm. Internode length: 1 cm. Stems are round, smooth and strong with very sparse, minute pubescence on the bottom of the main stems only. The shoots are initially upright but then fall outward, forming a dense canopy due to the many overlapping stems, Color: very dark purple/black (RHS 187A).

Petiole. Leaf petiole length varies; it averages 10.8 cm but goes up to 23 cm. Diameter: 0.4. Petiole texture is smooth. Color is 187A above and below.

Figure 1:
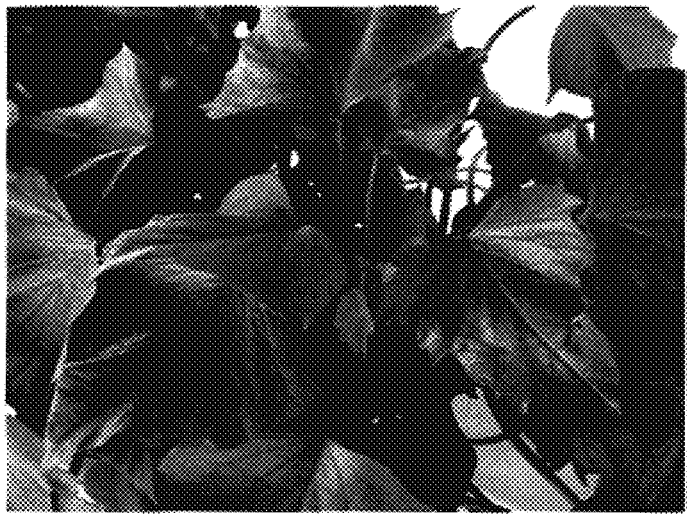
FIG. 1 is a color photograph showing both new and mature foliage produced by *Ipomoea batatas* 'Sweet Caroline Bewitched Purple'. The plant shown in FIG. 1 is 11 weeks of age.
Figure 2:
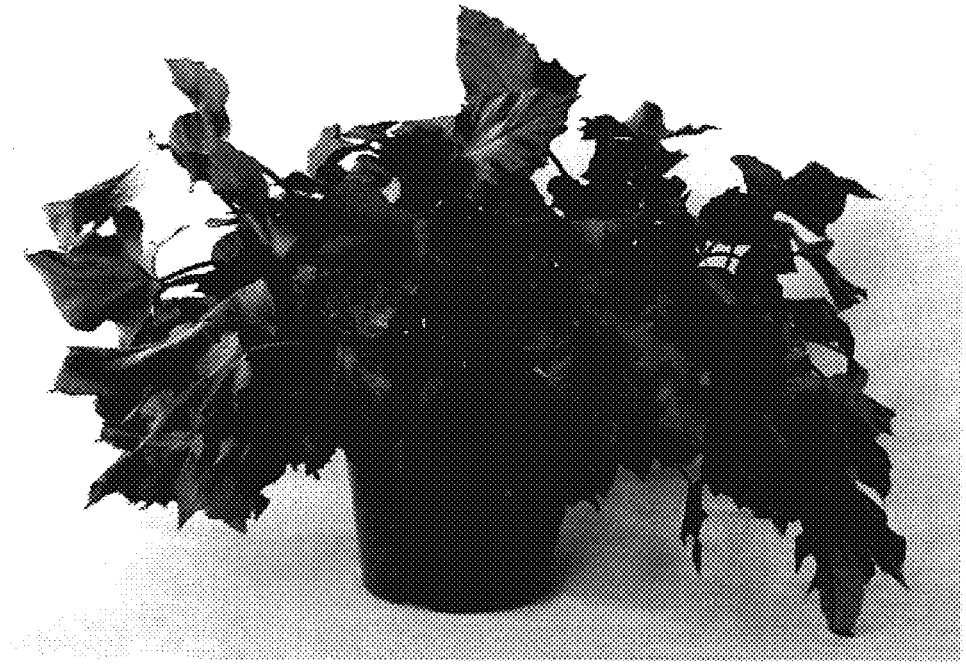
FIG. 2 is a color photograph of a typical plant of the *Ipomoea batatas* 'Sweet Caroline Bewitched Purple'. The plant shown in FIG. 2 is 11 weeks of age.

Foliage. Leaves are alternate and tend to spiral around the stems. They are simple and generally reniform with irregular projecting points (FIGS. 1 and 2). The number of leaves per stem varies with length; an average stem has ~26 leaves. The leaf tip is acuminate and the base is truncate. The leaf margins are slightly sinuate and nearly entire with irregular projections (toothing) around the leaf margins and especially at the base. Leaf length averages 9.5 cm (up to 11.5 cm) and leaf width averages 9 cm (up to 12 cm). The leaves have no pubescence. The venation pattern is palmate at the leaf base becoming arcuate toward the leaf tip. Color: Table 1.

TABLE 1

| Leaf Structure | Upper Surface | Lower Surface |
|---|---|---|
| Young Leaf | Bright yellow-green, RHS 144A | Bright yellow-green, RHS 144A |
| Mature Leaf | Dark green to dark purple, much darker than RHS 147A | Dark green to dark purple, a little more grey than RHS 187A |
| Vein | 187A | 187A |

Flowers. The production of flowers by 'Sweet Caroline Bewitched Purple' is very rare even under short day conditions and when produced the flowers are ephemeral (in most cases open only in the morning). Thus, despite best efforts, no flowers have been available for use in providing a description or photographs.

Figure 3:
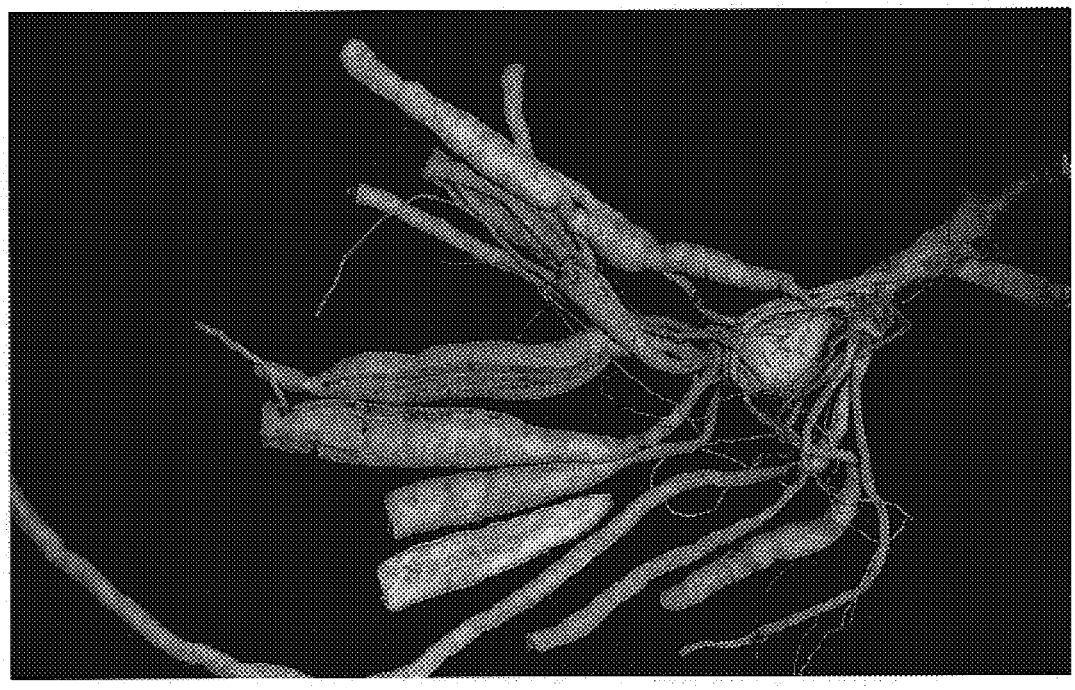
FIG. 3 is a color photograph showing typical storage roots produced by *Ipomoea batatas* 'Sweet Caroline Bewitched Purple' 123 days after planting. Plants were planted as five-hill plots spaced 30.5 cm apart in the row at the Horticultural Crops Research Station, Clinton, N.C. USA.

Below-Ground structure. Plants form small underground storage roots that are highly malformed and do not meet USDA Sweetpotato Storage Root Grade Standards (FIG. 3). Storage roots that do form typically possess cream colored skin (161A, 161B) with a cream colored flesh (158C) with light purple mottling (24B).

Growth conditions. *Ipomoea batatas* 'Sweet Caroline Bewitched Purple' has excellent vigor and growth rate. It is very adaptable to container culture. In locales with mild winter conditions, *Ipomoea batatas* 'Sweet Caroline Bewitched Purple' will grow perennially; otherwise it is an annual plant. Similar to cultivated sweetpotatoes, wind or rain rarely causes much damage to 'Sweet Caroline Bewitched Purple', but if damage does occur, the plant drops the damaged leaves and grows new shoots at nodes where the leaves were lost.

Disease or pest resistance. *Ipomoea batatas* 'Sweet Caroline Bewitched Purple' is susceptible to Sweetpotato Feathery Mottle Virus, white rust (caused by Albugo ipomoeae-panduratae) and damage by Japanese beetles.

Comparison with Other *Ipomoea batatas* Cultivars.

'Sweet Caroline Bewitched Purple' is very distinct based on leaf color, leaf shape and plant architecture (Table 2). Of the most common cultivars of ornamental sweetpotato, *Ipomoea batatas* 'Sweet Caroline Bewitched Purple' is best compared with the 'Sweet Caroline Purple' and 'Black Heart' cultivars. Like 'Sweet Caroline Purple', 'Sweet Caroline Bewitched Purple' is well-branched and moderate in size. 'Sweet Caroline Bewitched Purple' is more erect in plant habit than either 'Black Heart' or 'Sweet Caroline Purple'. Further, where 'Sweet Caroline Purple' has deeply lobed leaves and 'Black Heart' has heart-shaped leaves with slight toothing, 'Sweet Caroline Bewitched Purple' has pronounced toothing and no to slightly lobed leaves.

The patented strains used to produce 'Sweet Caroline Bewitched Purple' were NC547ORN (female parent) and 'Tricolor' (also called 'Pink Frost', male parent). 'Tricolor' is a pink, white and green variegated plant with modest vigor and moderately lobed leaves.

TABLE 1

| Characteristic | New Variety 'Sweet Caroline Bewitched Purple' | Comparison 1 'Sweet Caroline Purple' | Comparison 2 'Black Heart' |
|---|---|---|---|
| Plant Habit | Erect to Semi-erect | Moderately Compact | Trailing |
| Foliage Color | Greenish Purple | Dark Purple | Purple |
| Leaf Size | Moderate | Moderate | Moderate to Large |
| Leaf Shape | Well Toothed to Slightly Lobed | Deeply Lobed | Heart-Shaped to Slightly Toothed |

What is claimed is:

1. A new and distinct cultivar of *Ipomoea batatas* plant named 'Sweet Caroline Bewitched Purple', substantially as illustrated and described herein.

* * * * *